United States Patent [19]

Swithenbank

[11] 4,439,229
[45] Mar. 27, 1984

[54] SUBSTITUTED PHTHALIMIDES HERBICIDES

[75] Inventor: Colin Swithenbank, Perkasie, Pa.

[73] Assignee: Rohm and Haas Company, Philadelphia, Pa.

[21] Appl. No.: 375,248

[22] Filed: May 6, 1982

Related U.S. Application Data

[63] Continuation-in-part of Ser. No. 278,241, Jun. 29, 1981, abandoned.

[51] Int. Cl.$^3$ .................. A01N 43/38; C07D 209/48
[52] U.S. Cl. .......................................... 71/96; 71/90; 71/92; 71/94; 71/95; 544/236; 546/121; 548/453; 548/513; 548/549
[58] Field of Search ........................... 548/513; 71/96

[56] References Cited

U.S. PATENT DOCUMENTS 3,878,224  4/1975  Matsui et al. ................. 71/96
4,032,326  6/1977  Goddard ......................... 71/96
4,173,706 11/1979  Mathey et al. ................ 560/30

FOREIGN PATENT DOCUMENTS 49511  4/1982  European Pat. Off.
49508  4/1982  European Pat. Off.
8101135 10/1981 Netherlands.

OTHER PUBLICATIONS

Derwent Abstracts of J5 3073-557, NL 7117690, NL 7507233, J5 0142-730, DT 2604-989; J5 2083-554, J4 8099-338, J4 9006-121, BE 862-884, US 3,987-057, DT 2831-770, NL 8002-020.

Primary Examiner—Donald G. Daus
Assistant Examiner—M. C. Eakin
Attorney, Agent, or Firm—Terence P. Strobaugh

[57] ABSTRACT

Compounds of the formula:

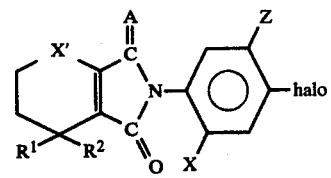

wherein A is O or S, halo is chloro, bromo or fluoro; X' is —CH$_2$—, O or S; X is hydrogen or halo; R$^1$ and R$^2$ are the same or different radicals selected from hydrogen or lower alkyl; and Z can be a variety of substituents and agronomically acceptable salts, esters and amides as well as other heterocyclic benzenes are disclosed as selective herbicides.

21 Claims, No Drawings

SUBSTITUTED PHTHALIMIDES HERBICIDES

This application is a continuation-in-part application of U.S. Ser. No. 278,241 filed June 29, 1982, now abandoned.

This invention relates to substituted phthalimides, compositions containing a substituted phthalmide, and to methods of controlling weeds.

Herbicides are broadly classified as either organic or inorganic chemicals. Since the introduction in 1932 of the first organic chemical, 2-methyl-4,6-dinitrophenyl, the search has continued for even better and more selective herbicides. It is believed that an ideal herbicide should give selective weed control, over a full growing season, with a single administration at a low rate of application of the herbicide. The ideal herbicide should be able to control all common weeds by killing them either as the seed, the germinating seed, the seedling or the growing plant. At the same time the ideal herbicide should be substantially non-phytotoxic to the crop or crops to which it is applied. Furthermore, the ideal herbicide should be decomposable or otherwise be dissipiated so as not to poison the soil for any long period of time. This ideal herbicide has yet to be discovered. The methods employed for killing weeds usually involves rotating the herbicides or by employing mixtures of herbicides in order to broaden the spectrum of weeds that may be controlled. Applicants have discovered novel compounds which can be added to the existing arsenal.

As stated previously, herbicides are broadly classified between organic and inorganic chemicals. Under organic chemicals there are approximately 19 different classifications of herbicides. See "Herbicides, Physiology, Biochemistry, Ecology", edited by L. J. Audus, Vol. 1 (1976), pages 5–15. The compounds of this invention fall within the class known as "miscellaneous heterocyclic compounds".

The following patents disclose compounds which also are believed to fall within the classification of "miscellaneous heterocyclic compounds". They are: Netherlands Pat. No. 7,117,690; Netherlands Pat. No. 7,507,233; Japanese Pat. No. 53073557; Japanese Pat. No. 50142730; German Pat. No. 2,604,989; Japanese Pat. No. 52093544; Japanese Pat. No. 48099338; Japanese Pat. No. 9006121; Belgian Pat. No. 862,844; German Pat. No. 2,831,770; U.S. Pat. No. 3,987,057 and Netherlands Pat. No. 8,002,020. Netherlands Pat. No. 8,002,020 discloses some of the starting materials employed to prepare some of the novel compounds of this invention.

In accordance with the present invention, there is provided phthalimides having the following structural formula:

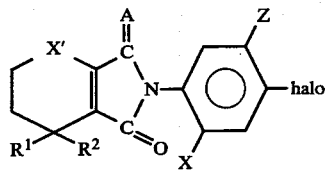

wherein A is O or S; $X^1$ is —$CH_2$—, O or S; $R^1$ and $R^2$ are the same or different radical selected from hydrogen or lower alkyl; X is hydrogen or halo, such as chloro, bromo, fluoro and the like; halo is chloro, bromo or fluoro and Z is carboxy, alkoxy-carbonyl, for example, lower alkoxycarbonyl such as methoxycarbonyl, ethoxycarbonyl, propoxycarbonyl, butoxycarbonyl, pentoxycarbonyl and the like, alkoxy-carbonylalkoxycarbonyl, for example, lower alkoxycarbonyl, butoxycarbonyl, pentoxycarbonyl and the like, alkoxycarbonylalkoxycarbonyl, for example, lower alkoxycarbonyl lower alkoxycarbonyl, such as methoxycarbonylmethoxycarbonyl, ethoxycarbonylpropoxy-carbonyl, methoxycarbonyl-1-methylmethoxycarbonyl, ethoxycarbonyl-1-methylmethoxycarbonyl, ethoxycarbonyl-1-ethylmethoxycarbonyl, acyloxy, for example, lower alkanoyloxy, such as acetyloxy, propionyloxy, butanoyloxy and the like; acylalkoxy, for example, lower alkanoyl lower alkoxy such as acetylmethoxy, propionylethoxy and the like; cyanoalkoxy for example cyano lower alkoxy such as cyanomethoxy, cyanoethoxy, cyanopropoxy, cyanobutoxy, cyanopentoxy, cyano-1-methylmethoxy, and the like; alkylthioalkoxy, for example, lower alkylthio lower alkoxy such as methyl-thiomethoxy, ethylthioethoxy, propylthiopropoxy and the like; alkoxycarbonylalkoxy, for example, lower alkoxycarbonyl lower alkoxy such as methoxycarbonylmethoxy, ethoxycarbonylethoxy, propoxycarbonylmethoxy and the like; alkoxycarbonylalkenyloxy, for example, lower alkoxycarbonyl lower alkenyloxy such as methoxycarbonyl-2-propenyloxy and the like; a 5- to 6-membered heterocyclic ring having from 1 to 3 heteroatoms selected from O, N or S such as 4-morpholino, 1-piperdyl, 3-thiazinyl, 1-(4-methylpiperazinyl), formylalkoxy, for example, formyl lower alkoxy such as formylmethoxy, formylethoxy, formylpropoxy, formylbutoxy, formylpentoxy and the like; haloalkoxy, for example, halo lower alkoxy such as chloroethoxy, bromoethoxy, fluoroethoxy, chlorobutoxy, and the like, mononuclear arylcarbonylalkoxy, for example, benzoyl lower alkoxy such as benzoylmethoxy, benzoylethoxy and the like; oxiranylalkoxy, for example, oxiranyl lower alkoxy such as oxiranylmethoxy, oxiranylethoxy and the like, amino, mono- or dialkylamino, such as mono- or di-lower alkylamino, hydrazino, mono- or dialkylhydrazino such as mono- or di lower alkylhydrazino, acylamino such as alkanoylamino, for example, lower alkanoylamino, alkoxyamino, such as, lower alkoxyamino, alkoxycarbonylamino, such as, lower alkoxycarbonylamino, mono- or dialkylaminocarbonylamino, such as mono- or di-lower alkylaminocarbonylamino, N-alkyl-N-lower alkoxy lower alkylaminocarbonylamino, haloalkylcarbonylamino, such as chloro lower alkylcarbonylamino, N-alkylsulfonylaminocarbonyl, such as N-lower alkylsulfonylaminocarbonyl; alkoxyalkoxycarbonyl, alkoxyalkoxy, N-alkylsulfonylamino, such as N-lower alkylsulfonylamino, mono- or dialkenylamino, such as mono- or di lower alkenylamino; mono- or di-alkynylamino, such as mono- or di lower alkynylamino, N-alkyl-N-alkenylamino, such as N-lower alkyl-N-lower alkenylamino, N-alkyl-N-alkylamino. Also included are the agronomically acceptable salts, esters and amides which are considered to be functionally equivalent to the parent compounds. For example, when Z is carboxy, salts such as the alkali metal and alkaline earth metal salts and amides, for example, lower alkyl and di lower alkylamides are considered to be functionally equivalent to the carboxy radical.

The term "lower" means straight or branched chain carbon containing radicals of up to 4 carbon atoms.

The preferred compounds of this invention relate to compounds having the following structural formula:

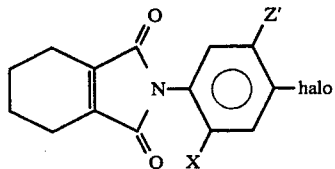

wherein halo is bromo or chloro, X' and Z' is lower alkoxycarbonyl, lower alkoxyalkoxycarbonyl, cyano lower alkoxy, lower alkylthioalkoxy, acetyl lower alkoxy, lower alkoxy lower alkoxy, halo lower alkoxy, formyl lower alkoxy, mono-lower alkylamino. These compounds exhibit not only herbicidal activity, but, more importantly, exhibit desired selectivity.

Most preferred are compounds wherein Z' is cyano lower alkoxy, lower alkylthio lower alkoxy or acetyl lower alkoxy, and X is hydrogen.

Examples of preferred compounds are as follows:

N-[3-(methoxycarbonyl)-4-chlorophenyl]-3,4,5,6-tetrahydrophthalimide;
N-[3-(1-methoxycarbonylethoxycarbonyl)-4-chlorophenyl]-3,4,5,6-tetrahydrophthalimide;
N-[3-(2-methoxycarbonylethoxycarbonyl)-4-chlorophenyl]-3,4,5,6-tetrahydrophthalimide;
N-[3-cyanomethoxy-4-chlorophenyl]-3,4,5,6-tetrahydrophthalimide;
N-[3-(1-cyanoethoxy)-4-chlorophenyl]-3,4,5,6-tetrahydrophthalimide;
N-[3-(1-cyanopropionoxy)-4-chlorophenyl]-3,4,5,6-tetrahydrophthalimide;
N-[3-(acetylmethoxy)-4-chlorophenyl]-3,4,5,6-tetrahydrophthalimide;
N-[3-(1-acetylethoxy)-4-chlorophenyl]-3,4,5,6-tetrahydrophthalimide;
N-[3-(methylthiomethoxy)-4-chlorophenyl]-3,4,5,6-tetrahydrophthalimide;
N-[3-(1-methylthioethoxy)-4-chlorophenyl]-3,4,5,6-tetrahydrophthalimide;
N-[3-(methoxymethoxy)-4-chlorophenyl]-3,4,5,6-tetrahydrophthalimide;
N-[3-(1-methoxyethoxy)-4-chlorophenyl]-3,4,5,6-tetrahydrophthalimide;
N-[3-[2-(1-methoxy)propionoxy]-4-chlorophenyl]-3,4,5,6-tetrahydrophthalimide;
N-[3-(formylmethoxy)-4-chlorophenyl]-3,4,5,6-tetrahydrophthalimide;
N-[3-(1-formylethoxy)-4-chlorophenyl]-3,4,5,6-tetrahydrophthalimide; and
N-[3-(N'-ethylamino)-4-chlorophenyl]-3,4,5,6-tetrahydrophthalimide.

Other compounds embraced by this invention include:

N-[3-(N'-methyl-N'-ethylamino)-4-chlorophenyl]-3,4,5,6-tetrahydrophthalimide;
N-[3-(N'-allylamino)-4-chlorophenyl]-3,4,5,6-tetrahydrophthalimide;
N-[3-(N'-methyl-N'-allylamino)-4-chlorophenyl]-3,4,5,6-tetrahydrophthalimide;
N-[3-(N'-ethyl-N'-allylamino)-4-chlorophenyl]-3,4,5,6-tetrahydrophthalimide;
N-[3-(N'-propynylamino)-4-chlorophenyl]-3,4,5,6-tetrahydrophthalimide;
N-[3-(N'-methyl-N'-propynylamino)-4-chlorophenyl]-3,4,5,6-tetrahydrophthalimide;
N-[3-N'-(2-methoxyethylamino)-4-chlorophenyl]-3,4,5,6-tetrahydrophthalimide;
N-[3-N'-methyl-N'-(2-methoxyethylamino)-4-chlorophenyl]3,4,5,6-tetrahydrophthalimide;
N-[3-N'-2-(1-methoxyethylamino)-4-chlorophenyl]-3,4,5,6-tetrahydrophthalimide;
N-[3-N'-(acetylmethylamino)-4-chlorophenyl]-3,4,5,6-tetrahydrophthalimide;
N-[3-N'-(1-acetylethylamino)-4-chlorophenyl]-3,4,5,6-tetrahydrophthalimide;
N-[3-N'-methyl-N'-(acetylmethylamino-4-chlorophenyl]-3,4,5,6-tetrahydrophthalimide;
N-[3-N'-(cyanomethylamino)-4-chlorophenyl]-3,4,5,6-tetrahydrophthalimide;
N-[3-N'-(1-cyanoethylamino)-4-chlorophenyl]-3,4,5,6-tetrahydrophthalimide;
N-[3-N'-methyl-N'-(cyanomethylamino)-4-chlorophenyl]-3,4,5,6-tetrahydrophthalimide;
N-[3-N'-(methylthiomethylamino)-4-chlorophenyl]-3,4,5,6 tetrahydrophthalimide;
N-[3-N'-(1-methylthioethylamino)-4-chlorophenyl]-3,4,5,6 -tetrahydrophthalimide; and
N-[3-N'-methyl-N'-(methylthiomethylamino)-4-chlorophenyl]-3,4,5,6-tetrahydrophthalimide.

Other compounds falling within the scope of this invention are illustrated by the following structural formulas.

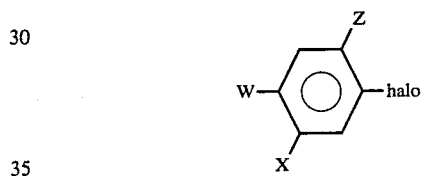

where W is a substituted heterocyclic of the II formula:

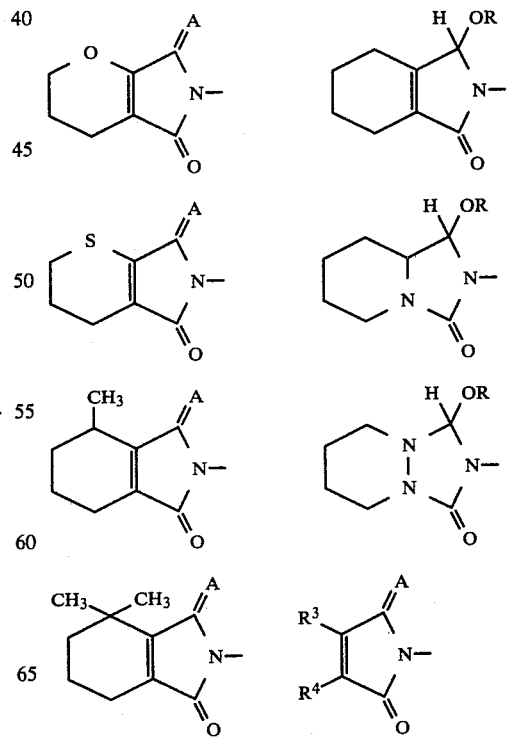

-continued

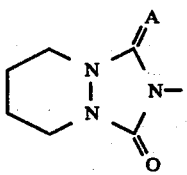

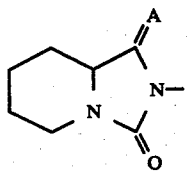

wherein A is O or S, R is hydrogen or lower alkyl, $R^3$ and $R^4$ are the same or different radicals selected from hydrogen, lower alkyl, lower alkenyl or lower alkynyl.

The products of this invention may be prepared by one of several routes depending on the particular heterocyclic desired and also on the nature of the Z substituent. The following process illustrates the preparation of the most preferred compounds:

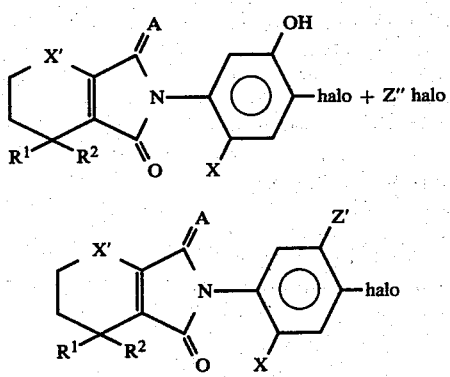

wherein A is O or S; X' is —CH$_2$— O or S, $R^1$ and $R^2$ are the same or different radicals selected from hydrogen or lower alkyl; Z' is Z"O and Z"O is an acyloxy, alkoxyalkoxy, acylalkoxy, cyanoalkoxy, alkylthioalkoxy, alkoxycarbonylalkoxy, alkoxycarbonylalkenylalkoxy, formylalkoxy, haloalkoxy, oxiranylalkoxy, arylcarboonylalkoxy. This reaction is generally conducted at a temperature in the range of from about room temperature to about 100° C. in a suitable inert polar solvent such as acetone, methylethylketone, acetonitrile, dimethyl formamide, dimethyl sulfoxide, dimethyl acetamide and the like.

The other procedure for preparing those compounds wherein Z contains a carbonyl radical joined to the benzene ring are prepared by treating an appropriately substituted anhydride with an appropriately substituted 3-aminobenzene compound. This reaction is generally conducted at a temperature in the range of from about room temperature to about 150° C. in a suitable solvent such as glacial acetic acid, propionic acid, xylene, toluene and the like. The following equation illustrates this process wherein A, $R^1$, $R^2$, X and Y are as defined above and Z''' is carboxy, alkoxycarbonyl, alkoxycarbonylalkoxycarbonyl and the like.

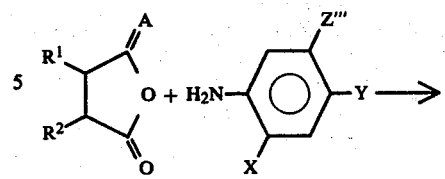

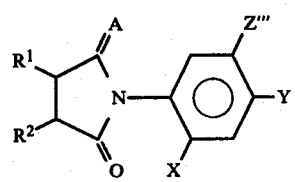

wherein $R^1$, $R^2$, X and Y are as defined above

Those compounds wherein the heterocyclic ring has two nitrogen atoms are prepared in the following manner:

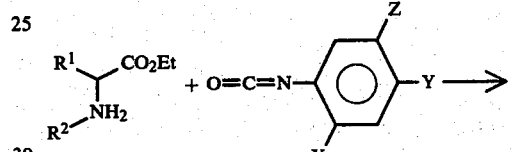

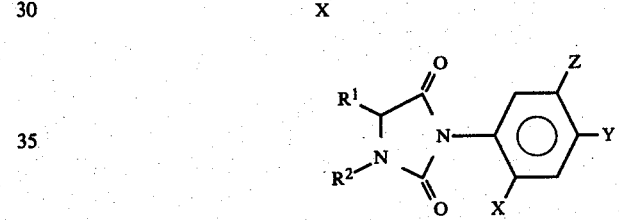

wherein $R^1$, $R^2$, X, Y and Z are as defined above. This reaction is conveniently conducted in an aqueous or alcoholic solution of a base. Examples of bases which may be employed include lithium hydroxide, sodium hydroxide, potassium hydroxide and the like. This reaction is conducted at a temperature in the range of from about 0° to about 100° C.

The preparation of those heterocyclic compounds containing three nitrogen atoms is illustrated by the following equation:

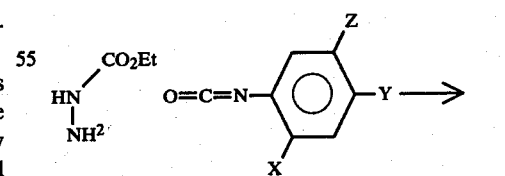

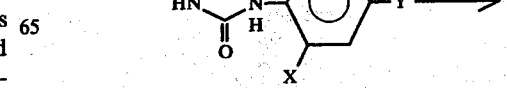

-continued

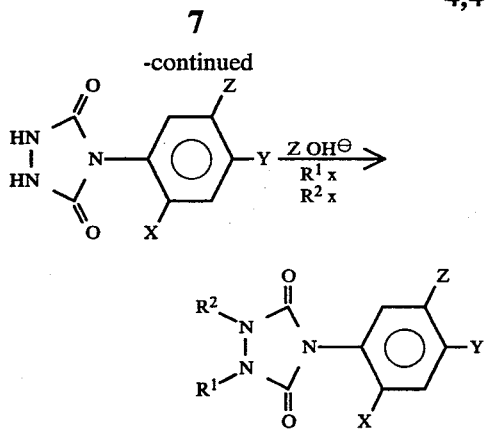

wherein $R^1$, $R^2$, X, Y and Z are as defined above. This reaction is generally conducted in the presence of an acid such as glacial acetic acid, propionic acid or p-toluene sulfonic acid in the presence of a suitable inert solvent such as ethers, aromatic solvents or halogenated hydro-carbons. The temperature of the reaction is generally in the range of from about 0° to about 150° C.

The starting materials are either known or may be prepared by methods well known to those skilled in the art.

The following illustrates one method of preparing amino and monosubstituted amino starting materials. Subsequent reaction will afford the disubstituted amino starting materials.

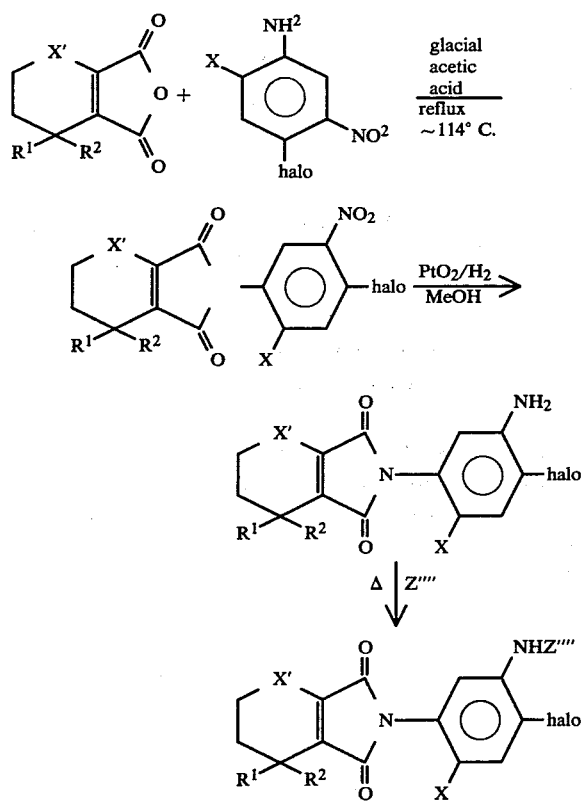

The reaction with Z'''' halo is conducted in a suitable inert solvent such as, acetonitrile, acetone, methylethylketone, dimethyl sulfoxide, dimethyl formamide, dimethyl acetamide and the like, at a temperature in the range of from room temperature to about 150° C.

The substituted phthalimide compounds (I, supra) of the invention are useful as preemergence and postemergence herbicides. Preemergence herbicides are ordinarily used to treat the soil by application either before seeding, during seeding, or after seeding and before the crop emerges.

The compounds of this invention are especially active as pre-emergence herbicides.

Among the crops on which the compounds of the invention can be advantageously employed are: cotton, soybeans, peanuts, beans, peas, carrots, corn, wheat, rice, and other cereal crops.

The compounds (I, supra) can be applied in any amount which will give the required control of weeds. A standard rate of application of the herbicides of the invention is in the range from about 0.02 to about 12 pounds of compound per acre. A preferred range is from about 0.1 to about 4 pounds per acre.

Under some conditions, the compounds (I, supra) may be advantageously incorporated into the soil or other growth medium prior to planting a crop. This incorporation can be by any convenient means, including simple mixing with the soil, applying the compounds to the surface of the soil and then disking or dragging into the soil to the desired depth, or by employing a liquid carrier.

The substituted phthalimides (I) and the other compounds illustrated above (II) falling within the scope of the invention can be applied to the growth medium or to plants to be treated ether neat or as a component of a herbicidal composition or formulation which also comprises an agronomically acceptable carrier. "Agronomically acceptable carrier" is any carried which can be used to dissolve, disperse or diffuse a herbicidal compound in the composition without imparing the effectiveness of the herbicidal compound and which by itself has no permanent detrimental effect on the soil, equipment, crops, or agronomic environment. Mixtures of the compounds of the invention may also be used in any of these herbicidal formulations. The herbicidal compositions of the invention can be either solid or liquid formulations or solutions. For example, the compounds can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used can be found in the John W. McCutcheon, Inc. publication "Detergents and Emulsifiers 1969 Annual."

Examples of solvents which are useful in the practice of this invention include alcohols, ketones, aromatic hydrocarbons, dimethyl formamide, dioxane, dimethyl sulfoxide, and the like. Mixtures of these solvents can also be employed. The concentration of the solution can vary from about 2% to about 98% of active product with a preferred range being from about 25% to about 75%.

For preparation of emulsifiable concentrates, the substituted phtalimides can be dissolved in organic solvents, such as toluene, xylene, methylated naphthalene, corn oil, pine oil, isophorone, cyclohexanone, methyl oleate, and the like, or in mixtures of these solvents, together with an emulsifying agent which permits dispersion in water. Suitable emulsifiers include, ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts or alkylbenzenesulfonates and the fatty alcohol sodium sulfates, having surfact-active properties can be used as emulsifiers either alone or in conjunction with an ethylene oxide reaction product. Flowable concentrates are formulated similarly to the emulsifiable concentrates and include, in addition to the above components, water and a stabilizing agent such as water-soluble salt of a poly-acrylic acid. The concentration of the active ingredient is emulsifiable concentrates is usually from about 10% to 60% and in flowable emulsion concentrates, can be as high as about 75%.

Wettable powders suitable for spraying, can be prepared by admixing the compound with a finely divided solid, such as clay, inorganic silicates and carbonates, and silicas and then incorporating wetting agents, sticking agents, and/or dispersing agents. The concentration of active ingredients in such formulations is usually in the range of from about 20% to about 98%, and preferable, from about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted from about 1% to about 10% use concentration.

Granular formulations can be prepared by impregnating a solid, such as granular fuller's earth, vermiculite, ground corn cobs, seed hulls, including bran or other grain- hulls, or similar material. A solution of one or more of the compounds in a volatile organic solvent can be sprayed or mixed with the granular solid and the solvent then removed by evaporation. The granular material can have any suitable size, with a preferable size in the range of from about 16 to 60 mesh. The compounds will usually comprise from about 2 to about 15% of the granular formulation.

The compounds of the invention (I and II) can also be mixed with fertilizers or fertilizing materials before their application. In one type of solid fertilizing composition in which the compounds can be used, particles of a fertilizer or fertilizing ingredients, such as ammonium sulfate, ammonium nitrate, or ammonium phosphate, can be coated with one or more of the phthalimides. The solid compounds and solid fertilizing material can also be admixed in mixing or blending equipment, or they can be incorporated with fertilizers in granular formulations. Any relative proportion of compound and fertilizer can be used which is suitable for the crops and weeds to be treated. The compound will commonly be from about 5% to about 25% of the fertilizing materials which promote the rapid growth of desired plants, and at the same time control the growth of undesired plants.

The compounds of the invention (I and II) can be applied as herbicidal sprays by methods commonly employed, such as conventional high-gallonage hydraulic sprays, low-gallonage sprays, airblast spray, aerial sprays, and dusts. For low volume applications, a solution of the compound is usually used. The dilution and rate of application will usually depend upon such factors as the type of equipment employed, the method of application, the area to be treated and the type and stage of development of the weeds.

For some applications, it may be desired to add one or more other herbicides along with the compounds of the invention. Examples of other herbicides which can be incorporated to provide additional advantages and effectiveness include:

Carboxylic Acids and Salts and Ester Derivatives Thereof 2,3,6-trichlorobenzoic acid, 2,3,5,6-tetrachlorobenzoic acid, 2-methoxy-3,5,6-trichlorobenzoic acid, 2-methoxy-3,5-dichlorobenzoic acid, 2-methyl-3,6-dichlorobenzoic acid, 2,3-dichloro-6-methylbenzoic acid, 2,4-dichlorophenoxyacetic acid, 2,4,5-trichlorophenoxyacetic acid, 2-methyl-4-chlorophenoxyacetic acid, 2-(2,4,5-trichlorophenoxy)propionic acid, 4-(2,4-dichlorophenoxy)butyric acid, 4-(2-methyl-4-chlorophenoxy)butyric acid, 2,3,6-trichlorophenylacetic acid, 3,6-endoxohexahydrophthalic acid, dimethyl 2,3,5,6-tetrachloroterephthalate, trichloroacetic acid, 2,2-dichloropropionic acid, 3-amino-2,5-dichlorobenzoic acid, and 2,3-dichloroisobutyric acid.

Carbamic Acid Derivatives ethyl N,N-di(n-propylthiocarbamate, propyl N,N-di(n-propyl)thiocarbamate, ethyl N-ethyl-N-(n-butyl) thiocarbamate, ethyl N-ethyl-N-(n-butyl)thiocarbamate, propyl N-ethyl-N-(n-butyl)thiocarbamate, 2-chloroallyl N,N-diethyldithiocarbamate, N-methyldithiocarbamic acid salts, ethyl 1-hexamethyleneiminecarbothiolate, isopropyl N-phenylcarbamate, isopropyl N(m-chloro-phenyl) carbamate, 4-chloro-2-butynyl N-(m-chloro-phenyl) carbamate, methyl N-(3,4-dichlorophenyl-carbamate, methyl-m-hydroxycarbanilate-m-methyl-carbanilate, and S-(4-chlorobenzyl)-N,N-diethylthiocarbamate.

Phenols dinitro-o-(sec-butyl)phenol and its salts, pentachlorophenol and its salts.

Substituted Ureas 3-(3,4-dichlorophenyl)-1,1-dimethylurea, 3-phenyl-1,1-dimethylurea, 3-(3,4-dichlorophenyl)-3-methoxy-1,1-dimethylurea, 3-(4-chlorophenyl)-3-methoxy-1,1-dimethylurea, 3-(3,4-dichlorophenyl)-1-n-butyl-1-methylurea, 3-(3,4-dichlorophenyl)-1-methoxy-1-methylurea, 3-(4-chlorophenyl)-1-methoxy-1-methylurea, 3-(3,4-dichlorophenyl)-1,1,3-trimethylurea, 3-(3,4-dichlorophenyl)-1,1-diethylurea, dichloral urea,[N'[4-(2-p-methylphenyl)ethoxy] phenyl]-N-methoxy-N-methylurea,1,1,3-trimethyl-3-(5-p-chlorobenzyl-thio-1,3,4-thiadyazol-2-yl)urea, and 3-[p-chlorophenoxy)phenyl]-1,1-dimethylurea.

Substituted Triazines 2-chloro-4,6-bis(ethylamino)-s-triazine, 2-chloro-4-ethylamino-6-isopropylamino-s-triazine, 2-methoxy-4,6-bis-(isopropylamino)-s-triazine, 2-methylmercapto-4,6-bis-(ethylamino)-s-triazine, 2-methylmercapto-4-ethylamino-6-isopropylamino-s-triazine, 2-chloro-4,6-bis(isopropylamino)-s-triazine, 2-methoxy-4,6-bis(e- thylamino)-s-triazine, 2-methoxy-4-ethylamino-6-isopropylamino-s-triazine, and 2-methylmercapto-4-(2-methoxyethyl-amino)-6-isopropylamino-s-triazine.

Diphenyl Ether Derivatives 2,4-dichloro-4'-nitrodiphenyl ether, 2,4,6-trichloro-4'-nitrodiphenyl ether, 2,4-dichloro-6-fluoro-4'-nitrodiphenyl ether, 2-chloro-4-trifluoromethyl-3'-carboxy-4'-nitrodiphenyl-ether and its salt and ester derivatives, 3-methyl-4'-nitrodiphenyl ether, 3,5-dimethyl-4'-nitrodiphenyl ether, 2,4'-dinitro-4-trifluoromethyl-diphenyl ether, 2,4-dichloro-3'-methoxy-4'-nitrodiphenyl ether, and sodium 5-(2-chloro-4-trifluoro-methyl-phenoxy)-2-nitrobenzoate.

Anilides

N-(3,4-dichlorophenyl)propionamide, N-(3,4-dichlorophenyl)methacrylamide, N-(3-chloro-4-methylphenyl)-2-methylpentamide, N-(3,4-dichlorophenyl)trimethylacetamide, N-(3,4-dichlorophenyl)B.B-dimethylvaleramide, N-isopropyl-N-phenylchloroacetamide and N-n-methoxy-methyl-N-(2,6-diethylphenyl)chloroacetamide, and 2-chloro-N-(2-ethyl-6-methylphenyl)-N-(2-methoxy-1-methylethyl)acetamide.

Uracils 5-bromo-3-s-butyl-6-methyluracil, 5-bromo-3-cyclohexyl-1,6-dimethyluracil, 3-cyclohexyl-5,6-trimethyleneuracil, 5-bromo-3-isopropyl-6-methyluracil and 3-tertbutyl-5-chloro-6-methyluracil.

Nitriles 2,6-dichlorobenzonitrile, diphenylacetonitrile, 3,5-dibromo-4-hydroxybenzonitrile, and 3,5-diiodo-4-hydroxybenzonitrile.

Other Organic Herbicides 2-chloro-N,N-diallylacetamide, N-(1,1-dimethyl-2-propynyl)-3,5-dichlorobenzamide, maleic hydrazide, 3-amino-1,2,4-triazole, monosodium methanearsonate, N,N-diallyl-2-chloroacetamide, disodium methanearsonate, N,N-dimethyl-B.B-diphenylacetamide, N,N-di(n-propyl)-2,6-dinitro-4-trifluoromethylaniline, N,N-di(n-propyl)-2,6-dinitro-4-methylaniline, N,N-di(n-propyl)-2,6-dinitro-4-methylsulfonylaniline, $N^3,N^3$-di-n-propyl-2,4-dinitro-6-trifluoromethyl-m-phenylenediamine, 3,5-dinitro-$N^4,N^4$-dipropylsulfanilamide, 4-isopropyl-2,6-dinitro-N,N-dipropylaniline, N-(2-chloroethyl)-2,6-dinitro-N-propyl-4-trifluoromethylaniline, O-(2,4-dichlorophenyl)-O-methylisopropylphosphoramidothioate, 4-amino-3,5,6-trichloropicolinic acid, 2,3-dichloro-1,4-naphthoquinone, di-(methoxythiocarbonyl)disulfide, and 3-isopropyl-1H-2,1,3-benzothiadiazine(4)3H-one-2,2 dioxide.

The following examples illustrate the products of this invention and methods for preparing them. However, it should be understood that the other products falling within the generic description can be prepared in a similar manner.

Example 1

A solution of 9.1 g (0.06 mole) of 3,4,5,6-tetrahydrophilic anhydride and 11.1 g (0.06 mole) of methyl 2-chloro-5-aminobenzoate dissolved in glacial acetic acid (30 ml.) is vigorously refluxed for one hour. The reaction mixture is cooled to room temperature and the crude product is collected by filtration, washed with water and then dried to afford 14.9 g of N-[3-methoxycarbonyl-4-chlorophenyl]-3,4,5,6-tetrahydrophthalimide m.p. 113°–115° C.

By following substantially the procedure described in Example 1 other compounds, wherein Z contains a carbonyl attached directly to the benzene ring, may be prepared in a similar manner. The following table taken together with the structure identified as "Formula I" illustrate other compounds prepared by this method.

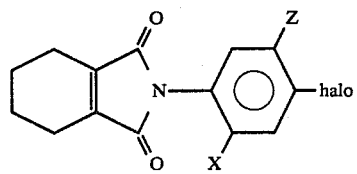

Formula I

| Example No. | X | Halo | Z | m.p. °C. | Molecular Formula |
|---|---|---|---|---|---|
| 2 | H | Cl | —CO$_2$H | 239–241 | C$_{15}$H$_{12}$ClNO$_4$ |
| 3 | H | Cl | —CO$_2$Me | 113–115 | C$_{16}$H$_{14}$ClNO$_4$ |
| 4 | H | Cl | —CO$_2$CH$_2$CO$_2$Me | 113–117 | C$_{18}$H$_{16}$ClNO$_6$ |
| 5 | H | Cl | —CO$_2$CH(Me)CO$_2$Me | oil | C$_{19}$H$_{18}$ClNO$_6$ |
| 6 | H | Cl | —CO$_2$CH(Et)CO$_2$Et | oil | C$_{21}$H$_{22}$ClNO$_6$ |
| 7 | H | Cl | —CO$_2$(CH$_2$)$_3$CO$_2$Et | oil | C$_{21}$H$_{22}$ClNO$_6$ |

Example 8

N-[3-(3-Ethoxycarbonylpropoxy-4-chlorophenyl]3,4,5,6-tetrahydrophthalimide

Step A: N-(3-Hydroxy-4-chlorophenyl)-3,4,5,6-tetrahydrophthalimide

Employed 47.5 g of 3-hydroxy-4-chloroaniline (0.33 mol); 38.2 of 3,4,5,6-tetrahydrophthalic anhydride (0.25 mol) and 350 ml of glacial acetic acid.

Procedure:

To a 500 ml. round bottom flask is added the crude aniline together with the anhydride and glacial acetic acid. The mixture is refluxed for 2 days. Added water and poured the reaction mixture into a separatory funnel, added concentrated HCl, extracted with ether and dried over anhydrous MgSO$_4$. Total crude yield is 42.4 g (re-crystallized a 1.0 g. sample from methanol and water to obtain 0.7 g of product, m.p., 220°–225° C. The NMR and I.R. agree with expected product structure.

Step B: N-[3-(3-Ethoxycarbonylpropoxy-4-chlorophenyl]-3,4,5,6-tetrahydrophthalimide To a 100 ml round bottomed flask equipped with a reflux condenser, magnetic stirrer and heating mantle is added 5.0 g of potassium carbonate, 5.0 g of N-(3-hydroxy-4-chlorophenyl)-3,4,5,6-tetrahydrophthalimide and 80 ml of methylethyl ketone. To this is added 2.9 ml. of ethyl 4-bromobutyrate and the mixture refluxed. Thin layer chromatography showed that the reaction is incomplete. Added more ethyl 4-bromobutyrate (2–3 ml.) and potassium carbonate (2.0 g) and refluxed for an additional 1 hour. Removed solvent under reduced pressure and added ether to the residue. Washed successively with 30 ml of 2 M sodium hydroxide, 15 ml. of 6 M sodium hydroxide and 20 ml of saturated salt solution. Removed ether to obtain 6 g of N-[3-(3-ethoxycarbonylpropoxy-4-chloro-phenyl]-3,4,5,6-tetrahydrophthalimide. NMR and IR confirm product obtained.

In substantially the same manner as described in example 8 and by employing the appropriate starting materials, the following products can be prepared.

| Example No. | X | Halo | Z | m.p. °C. |
|---|---|---|---|---|
| 9 | H | Cl | —OCOCH$_3$ | oil |
| 10 | H | Cl | —OCH$_2$CN | 110–118 |
| 11 | H | Cl | —OCH$_2$SCH$_3$ | oil |
| 12 | H | Cl | —OCH$_2$COCH$_3$ | 100–105 |
| 13 | H | Cl | —OCH$_2$CH—CH$_2$ (epoxide) | — |
| 14 | H | Cl | —OCH$_2$CO$_2$Me | oil |
| 15 | Cl | Cl | —OCH(Me)CO$_2$Me | oil |
| 16 | H | Cl | —OCH$_2$CH=CHCO$_2$Me | oil |
| 17 | H | Cl | —O(CH$_2$)$_3$CO$_2$Et | oil |
| 18 | H | F | —OCH(Me)CN | — |
| 19 | H | Cl | —OCH$_2$CHO | — |
| 20 | H | Cl | —OCH$_2$OCH$_3$ | — |
| 21 | H | Br | —OCH$_2$CH$_2$OCH$_3$ | — |
| 22 | Br | Cl | —OCH$_2$CH$_2$Cl | — |
| 23 | H | Cl | —CO$_2$Na | — |
| 23A | F | Cl | —OCH$_3$CN | — |
| 24 | H | Cl | —OCH(CH$_3$)CN | oil |
| 25 | H | Cl | —OCH$_2$CH$_2$OCH$_3$ | oil |
| 26 | H | Cl | —OCH$_2$CH$_2$Cl | 94–100 |
| 27 | H | Cl | —OCH(CH$_3$)COCH$_3$ | 86–92 |
| 28 | H | Cl | —OCH(CH$_3$)SCH$_3$ | oil |
| 29 | H | Cl | —OCH(CH$_2$CH$_3$)CN | oil |
| 30 | H | Br | —OCH(CH$_3$)CN | 113–116 |
| 31 | H | Cl | —OCH$_2$CF$_3$ | 91.5–96 |
| 32 | H | CH$_3$ | —OCH(CH$_3$)CN | 149 |

Example 33

N-(3-Ethylamino-4-chlorophenyl)-3,4,5,6-tetrahydrophthalimide

Used:
2.5 g of 3-ethylamino-4-chloroaniline;
2.1 g of 3,4,5,6-tetrahydrophthalic anhydride and
2–3 ml of glacial acetic acid.
Procedure
In a 50 ml round bottomed flask, combined above ingredients and refluxed overnight under nitrogen.
Work up=Added water and extracted with 3 portions of methylene chloride (CH$_2$Cl$_2$). Washed three times with 2 M NaOH (to remove acetic acid). Washed with brine, stripped the CH$_2$Cl$_2$ to afford 4.0 g of crude product which was recrystallized from ethyl acetate and hexane to yield 2.8 g of product as a green solid, m.p. 120°–127° C.

Example 34

N-(3-Dimethylamino-4-chlorophenyl-3,4,5,6-tetrahydrophthalimide

Step A: N-(3-nitro-4-chlorophenyl)-3,4,5,6-tetrahydrophthalimide

To a stirred mixture of 25 g of 3,4,5,6-tetrahydrophthalic anhydride and 150 ml. of glacial acetic acid, under N$_2$, is added 31.2 g of 4-chloro-3-nitroamiline and the mixture heated to reflux overnight. The reaction is cooled to room temperature and the resulting precipitate filtered and washed with hexane to yield 45 g of product.

Step B: N-(3-Amino-4-chlorophenyl)-3,4,5,6-tetrahydrophthalimide

To a solution of 40 g of N-(3-nitro-4-chlorophenyl)-3,4,5,6-tetrahydrophthalimide in 900 ml. of MeOH and 100 ml. of EtOAc in a hydrogenation bottle is added 0.5 g PtO$_2$. The bottle is purged with hydrogen then pressurized to 50 psig and shaken until the required amount of H$_2$ was used. The reaction mixture was filtered through celite, washed well with CH$_2$Cl$_2$ and the combined organic phases concentrated in vacuo to yield 29 g of the product. This product was used without further purification in subsequent transformations.

Step C: N-(3-Dimethylamino-4-chlorophenyl)-3,4,5,6-tetrahydrophthalimide

To a stirred solution of 3.5 g of N-(3-amino-4-chlorophenyl)-3,4,5,6-tetrahydrophthalimide and 3.5 g powdered K$_2$CO$_3$ in 70 ml. acetone under N$_2$ is added 5 ml CH$_3$I and the mixture heated to reflux overnight. Two additional portions of CH$_3$I are added (5 ml each) during the course of the reaction. The reaction mixture is cooled to room temperature filtered, and the solvent removed under vacuum. The crude product is dissolved in CH$_2$Cl$_2$ and passed through a plug of alumina and the solvent stripped off. The partially purified product is further purified by MPLC eluting with 33% EtOAc/hexane, MP124°–7° C.

The following procedure can be employed to prepare other amino and substituted amino compounds:

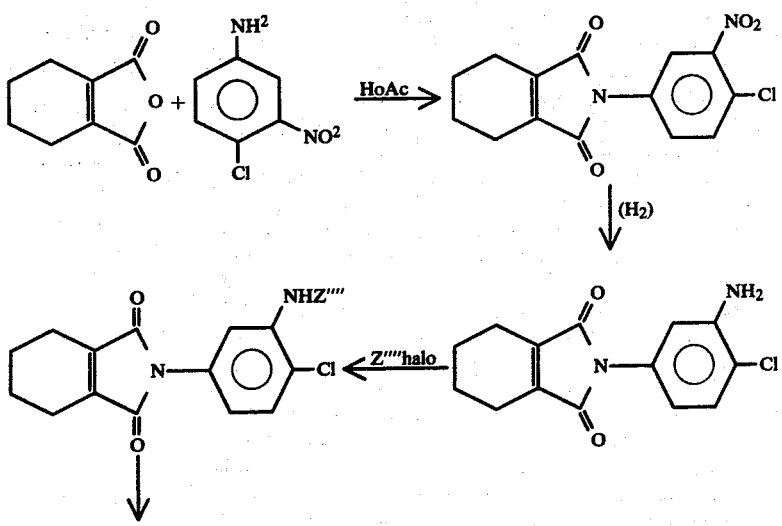

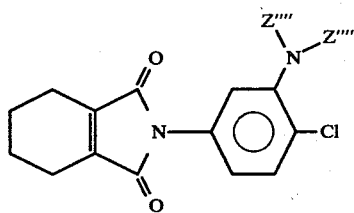

| Example No. | Z'''' | Z'''' | m.p. °C. |
|---|---|---|---|
| 35 | H | NH₂ | — |
| 36 | CH₃ | H | — |
| 37 | CH₃CO— | H | — |
| 38 | CH₃O— | H | — |
| 39 | CH₃OCO— | H | — |
| 40 | CH₃NHCO— | H | — |
| 41 | CH₃CH₂CO— | H | — |
| 42 | CH₃SO₂— | H | — |
| 43 | CH₃OCH₂N(CH₃)CO— | H | — |
| 44 | CH=CHCH₂— | CH=CHCH₂— | oil |
| 45 | C₂H₅— | CH=CHCH₂— | — |
| 46 | C₃H₅— | C≡CCH₂— | — |
| 47 | C₂H₅— | H | 130-137 |
| 48 | ClCH₂CO— | H | 111-118 |

Example 49

N-(4-Chlorophenyl)-3-oxa-6-thia-3,4,5,6-tetrahydrophthalimide

To a stirred, room temperature solution of 1.6 g sodium methoxide in 50 ml methanol is added 1.17 g 2-mercaptoethanol. The solution is stirred for 15 min. then 4.5 g of N-(4 chlorophenyl)-dichloromalemide is added in one portion. The reaction mixture is complete in one hour. The solvent is removed and the resulting solid is triturated with ether. The combined ether washing are extracted with water (2×40 ml) and dried over Na₂SO₄. Filtration through celite and removal of the solvent affords a yellow oil. The oil is purified by MPLC eluting with 30% EtOAc/hexanes to yield 0.5 g of the product as a pale yellow solid; m.p. 158° C.

Example 50

N-[3-2-(Cyanoethyl)-4-chlorophenyl]-3,4,5,6-tetrahydrophthalimide

Step A: 2-Chloro-5-nitrocinnamylnitrile

To a slurry of 20.5 g of 2-chloro-5-nitroaniline in 22 ml. H₂O and 45 ml. of conc. HCl at room temperature was slowly added a conc. aqueous solution of NaNO₂ (9.0 g NaNO₂). The slurry was stirred at room temperature for 30 minutes. The resulting diazonium salt was added slowly and portionwise to a stirred room temperature mixture of 10 ml. of HOAC/80 ml. acetone/30 ml. 25% aqueous NaOH containing 3.5 g CuCl and 9.4 ml. acrylonitrile. After addition of the diazonium was complete, the slurry was warmed to 35°-45° C. for 1.5 hours during which time N₂ evolution ceased. The reaction mixture was washed well with CH₂Cl₂, the CH₂Cl₂ washings combined, filtered, and dried with Mg8O₄. The solvent was stripped off after filtration to yield 14 g of the intermediate product. All of this material was added to refluxing Et₃N. The reaction was heated at reflux for an additional 15 min, cooled to room temperature and CH₂Cl₂ added. The organic phase was washed with cold dilute H₂8O₄ until all of the Et₃N had been removed from the organic phase. The CH₂Cl₂ solution was dried with Mg8O₄, filtered and the solvent removed to yield 10.2 g of the desired product. This material was used in subsequent reaction s without further purification.

Step B: 3-(2-Cyanoethyl)-4-chloroaniline

To a solution of 10.2 g of 2-chloro-5-nitro cinnamylnitrite in 150 ml. 1:1 EtOAc/MeOH was added 0.5 g PtO₂ in a hydrogenation bottle. The bottle was purged with H₂, pressurized to 50 psig and shaken until the calculated amount of H₂ had been used. The reaction mixture was filtered through celite and washed well with EtOAc. Concentration of the solution gave 7.9 g. of the desired aniline. This product was used in the subsequent reaction without further purification.

Step C: N-[3-(2-Cyanoethyl)-4-chlorophenyl]-3,4,5,6-tetrahydrophthalimide

To a stirred slurry of 5.0 g of 3,4,5,6-tetrahydrophthalic anhydride in 5 ml. of glacial acetic acid under N₂ is added 7.5 g of 3-(2-cyanoethyl)-4-chloroaniline and the mixture heated to reflux for 2 hours. The reaction mixture is cooled to room temperature, water is added together with several mls. of conc. HCl and the mixture extracted with ether. The combined ether extracts are washed with saturated brine and then dried over MgSO₄. Filtration and removal of the solvent yielded 8.9 g of a brown oil. The oil is dissolved in CH₂Cl₂, passed through a plug of alumina, the solvent removed, and then further purified by MPLC eluting with 25% EtOAc/hexanes to yield the product as a yellow solid, m.p. 87°–97° C.

One skilled in the art will appreciate that the above examples are merely illustrative and are capable of a wide variation and modification without departing from the spirit of this invention as defined by the following claims.

Test Procedure

This example shows the procedure for determining herbicidal activity of the compounds of the invention by employing the following representative weed species:

|  |  |  | Approx. No. Seeds |
|---|---|---|---|
| Monocots | Barnyardgrass | (*Echinochloa crusgalli*) | 25 |
|  | Downybrome | (*Bromus tectorum*) | 20 |
|  | Foxtail | (*Setaria spp*) | 25 |
|  | Johnsongrass | (*Sorghum Halepenese*) | 25 |
|  | Nutsedge | (*Cyperus esculentus*) | 5 |
|  | Wild Oat | (*Avena fata*) | 20 |
| Dicots | Cocklebur | (*Xanthium pensylvanicum*) | 3 |
|  | Marigold | (*Tagetes spp*) | 15 |
|  | Morning Glory | (*Ipomoea spp*) | 10 |
|  | Tomato | (*Lycopersicon esculentum*) | 15 |
|  | Velvetleaf | (*Abutilon theophrasti*) | 15 |
|  | Sicklepod | (*Cassia* | 6 |

-continued

| Approx. No. Seeds |
|---|
| *obtusifolia*) |

The following test procedure is employed. Seeds of the above species are planted in soil in trays (approx. 7"×10½"×3"). For preemergence tests, the trays are sprayed with the test compound immediately after planting. For postemergence tests, the seeds are allowed to germinate and after growing in the greenhouse for two weeks, the growing plants are treated with the test compound. The compound to be evaluated is dissolved in acetone or water and sprayed over the trays using a carrier volume equivalent to 50 gallons per acre at the rate of application (in pounds per acre, lb/A) specified in the table. About two weeks after application of the test compound, the state of growth of the plants is observed and the phytotoxic effect of each compound determined as follows: each species is evaluated on a scale of 1–100 in which 0=no activity and 100=total kill and the results for the monocots (M) and dicots (D) separately averaged. The results obtained for the compounds of the invention tested at 2 lb/A, ½ lb/A and ⅛ lb/A indicate that the compounds are selective herbicides.

where W is a substituted heterocyclic selected from:

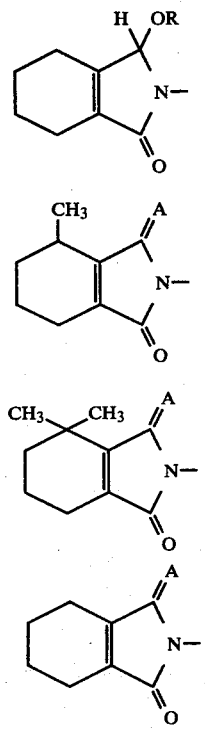

HERBICIDAL DATA

| Exam. No. | Preemergence | | | | Postemergence | | | |
|---|---|---|---|---|---|---|---|---|
| | ½ lb./A. | | 2 lbs./A. | | ½ lb./A. | | 2 lbs./A. | |
| | MONOCOT | DICOT | MONOCOT | DICOT | MONOCOT | DICOT | MONOCOT | DICOT |
| 2 | 2 | 4 | 2 | 20 | 8 | 28 | 3 | 70 |
| 3 | 0 | 23 | 28 | 40 | 5 | 65 | 10 | 78 |
| 4 | 0 | 0 | 0 | 0 | 0 | 58 | 3 | 86 |
| 5 | 5 | 6 | 10 | 66 | 27 | 98 | 36 | 100 |
| 6 | 0 | 0 | 6 | 0 | 0 | 32 | 17 | 96 |
| 7 | 0 | 0 | 0 | 0 | 0 | 84 | 0 | 86 |
| 9 | 8 | 32 | 17 | 61 | 16 | 33 | 19 | 47 |
| 10 | 21 | 72 | 52 | 83 | 11 | 92 | 21 | 99 |
| 11 | 31 | 78 | 54 | 79 | 9 | 79 | 19 | 93 |
| 12 | 39 | 78 | 46 | 83 | 5 | 52 | 17 | 86 |
| 13 | 11 | 43 | 26 | 60 | 4 | 53 | 5 | 81 |
| 15 | 2 | 34 | 18 | 46 | 2 | 56 | 4 | 56 |
| 16 | 16 | 40 | 0 | 45 | 0 | 0 | 18 | 0 |
| 17 | 3 | 63 | 5 | 78 | 5 | 76 | 4 | 96 |
| 24 | 57 | 84 | 89 | 100 | 26 | 100 | 58 | 100 |
| 23 | 16 | 49 | 9 | 45 | 0 | 0 | 18 | 0 |
| 25 | 46 | 50 | 69 | 68 | 23 | 67 | 30 | 83 |
| 26 | 40 | 42 | 71 | 87 | 18 | 78 | 34 | 85 |
| 27 | 32 | 63 | 70 | 83 | 33 | 78 | 43 | 78 |
| 28 | 42 | 95 | 73 | 98 | 22 | 89 | 28 | 96 |
| 29 | 49 | 75 | — | — | 8 | 65 | — | — |
| 30 | 53 | 83 | 64 | 98 | 6 | 65 | 8 | 76 |
| 31 | 12 | 24 | 38 | 64 | 8 | 36 | 13 | 38 |
| 32 | 42 | 62 | 48 | 85 | 3 | 40 | 9 | 63 |
| 33 | 12 | 18 | 16 | 15 | 0 | 18 | 0 | 23 |
| 44 | 2 | 18 | 20 | 33 | 3 | 13 | 5 | 23 |
| 47 | 43 | 75 | 59 | 73 | 27 | 76 | 29 | 88 |
| 48 | 0 | 3 | 0 | 3 | 2 | 2 | 3 | 3 |
| 50 | 7 | 37 | 31 | 60 | 2 | 50 | 11 | 51 |

What is claimed is:

1. A compound of the formula

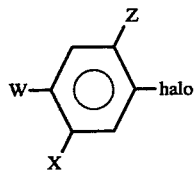

wherein A is O or S; halo is chloro, bromo or fluoro; $R^1$ and $R^2$ are the same or different radicals selected from hydrogen or lower alkyl; X is hydrogen or halo; Z is cyanoalkoxy; R is hydrogen or lower alkyl.

2. A compound according to claim 1 of the formula:

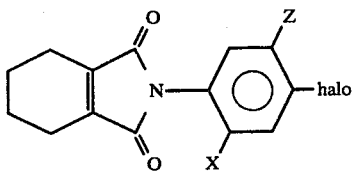

wherein X is hydrogen or halo; and Z is cyanoalkoxy.

3. The compound of claim 2 of the formula:

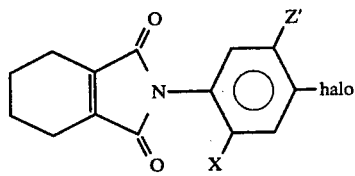

wherein halo is chloro or bromo; X is halo or hydrogen; and Z' is cyano lower alkoxy.

4. A compound according to claim 3 wherein Z' is cyano lower alkoxy and X is hydrogen.

5. A compound according to claim 4 named N-[3-(1-cyanoethoxy)-4-chlorophenyl]3,4,5,6-tetrahydrophthalimide.

6. A compound according to claim 4 named N-[3-(1-cyanoethoxy)-4-bromophenyl]3,4,5,6-tetrahydrophthalimide.

7. A compound according to claim 4 named N-[3-(1-cyanopropoxy)-4-chlorophenyl]3,4,5,6-tetrahydrophthalimide.

8. A herbicidal composition comprising a herbicidally effective amount of a compound according to claim 1 in an agronomically acceptable carrier.

9. A herbicidal composition comprising a herbicidally effective amount of a compound according to claim 2 in an agronomically acceptable carrier.

10. A herbicidal composition comprising a herbicidally effective amount of a compound according to claim 3 in an agronomically acceptable carrier.

11. A herbicidal composition comprising a herbicidally effective amount of a compound according to claim 4 in an agronomically acceptable carrier.

12. A herbicidal composition comprising a herbicidally effective amount of a compound according to claim 5 in an agronomically acceptable carrier.

13. A herbicidal composition comprising a herbicidally effective amount of a compound according to claim 6 in an agronomically acceptable carrier.

14. A herbicidal composition comprising a herbicidally effective amount of a compound according to claim 7 in an agronomically acceptable carrier.

15. A method for controlling weeds which comprises applying to the weed or a growth medium therefor an effective amount of the compound of claim 1.

16. A method for controlling weeds which comprises applying to the weed or a growth medium therefor an effective amount of the compound of claim 2.

17. A method for controlling weeds which comprises applying to the weed or a growth medium therefor an effective amount of the compound of claim 3.

18. A method for controlling weeds which comprises applying to the weed or a growth medium therefor an effective amount of the compound of claim 4.

19. A method for controlling weeds which comprises applying to the weed or a growth medium therefor an effective amount of the compound of claim 5.

20. A method for controlling weeds which comprises applying to the weed or a growth medium therefor an effective amount of the compound of claim 6.

21. A method for controlling weeds which comprises applying to the weed or a growth medium therefor an effective amount of the compound of claim 7.

* * * * *